(12) United States Patent
Morimoto et al.

(10) Patent No.: US 7,772,406 B2
(45) Date of Patent: Aug. 10, 2010

(54) PROCESS FOR PRODUCTION OF BENZYLOXYPYRROLIDINE DERIVATIVE, AND PROCESS FOR PRODUCTION OF HYDROCHLORIDE SALT POWDER OF OPTICALLY ACTIVE BENZYLOXYPYRROLIDINE DERIVATIVE

(75) Inventors: Masao Morimoto, Nagoya (JP); Atsushi Yamakawa, Nagoya (JP)

(73) Assignee: Toray Fine Chemicals Co., Ltd., Chiba (JP)

( * ) Notice: Subject to any disclaimer, the term of this patent is extended or adjusted under 35 U.S.C. 154(b) by 1 day.

(21) Appl. No.: 12/084,316

(22) PCT Filed: Oct. 30, 2006

(86) PCT No.: PCT/JP2006/321611

§ 371 (c)(1),
(2), (4) Date: Apr. 30, 2008

(87) PCT Pub. No.: WO2007/052578

PCT Pub. Date: May 10, 2007

(65) Prior Publication Data

US 2009/0093643 A1    Apr. 9, 2009

(30) Foreign Application Priority Data

Oct. 31, 2005  (JP)  ............................. 2005-315791
Nov. 11, 2005  (JP)  ............................. 2005-328187
Jun. 13, 2006  (JP)  ............................. 2006-163076

(51) Int. Cl.
  *A61K 31/40*    (2006.01)
  *C07D 207/12*   (2006.01)
(52) U.S. Cl. ...................... 548/541; 514/424
(58) Field of Classification Search ................. 548/541; 514/424
  See application file for complete search history.

(56) References Cited

U.S. PATENT DOCUMENTS 5,037,841 A * 8/1991 Schohe et al. ............... 514/373
5,854,268 A   12/1998 Baker et al. ................. 514/383

FOREIGN PATENT DOCUMENTS

WO    2004/099137 A1    11/2004
WO    2005/094897 A2    10/2005
WO    2005/097087 A2    10/2005
WO    WO-2005/009487 A2 *  10/2005
WO    WO-2005/097087 A2 *  10/2005

OTHER PUBLICATIONS

Sternfield, Francine et al., "Synthesis and Serotonergic Activity of 3-[2-(Pyrrolidin-1-yl)ethyl]indoles: Potent Agonists for the h5-HT$_{1D}$ Receptor with High Selectivity over the h5-HT$_{1B}$ Receptor", *J. Med. Chem.* 1999, 42, pp. 677-690.

* cited by examiner

*Primary Examiner*—Joseph K. McKane
*Assistant Examiner*—Janet L Coppins
(74) *Attorney, Agent, or Firm*—Kubovcik & Kubovcik

(57) ABSTRACT

Provided are: a process for production of a benzyloxypyrrolidine derivative in high yield and safety, and a process for production of a hydrochloride powder of a benzyloxypyrrolidine derivative in high yield and safety; the process for production of a benzyloxypyrrolidine derivative expressed by the general formula (2) [Chemical formula 2], in reacting a pyrrolidinol derivative represented by the general formula (1) [Chemical formula 1] with a benzyl halide derivative in the presence of an alkali metal hydroxide, wherein the reaction is carried out in either of the following conditions A or B; condition A: an aprotic polar solvent, and condition B: an aliphatic ether solvent containing a phase transfer catalyst:

[Chemical formula 1]

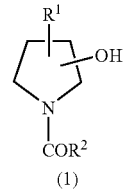

(1)

[Chemical formula 2]

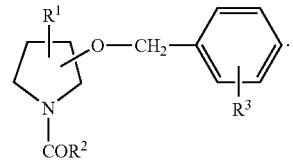

(2)

9 Claims, No Drawings

PROCESS FOR PRODUCTION OF BENZYLOXYPYRROLIDINE DERIVATIVE, AND PROCESS FOR PRODUCTION OF HYDROCHLORIDE SALT POWDER OF OPTICALLY ACTIVE BENZYLOXYPYRROLIDINE DERIVATIVE

TECHNICAL FIELD

The present invention relates to a process for production of a benzyloxypyrrolidine derivative, and a process for production of a hydrochloride powder of an optically active benzyloxypyrrolidine derivative.

BACKGROUND ART

Benzyloxypyrrolidine derivatives, above all, optically active benzyloxypyrrolidine derivatives are useful compounds as various medicine intermediates, and many processes for production thereof have been known. In particular, when used as a starting material for a medical product, it is essential to procure a high-purity substance.

First, a process for production of a benzyloxypyrrolidine derivative will be described. It is a general method that a nitrogen-containing cyclic alcohol derivative is reacted with benzyl halide in a basic condition. As specific examples, a reaction of 1-tert-butoxycarbonyl-3-hydroxypyrrolidine with benzyl halide is mentioned. In this reaction, halogenation is carried out with benzyl bromide in the presence of sodium hydride (Patent document 1, Non-patent document 1), but it can be said that implementation in an industrial scale is difficult because of using combustible substances such as sodium hydride. Further, as a method for production of a benzyloxypyrrolidine derivative by benzylation of a piperinol derivative, a reaction example in the presence of tetrabutylammonium iodide catalyst is reported (Patent document 2), there is used a benzyl chloride of 11.5 times by mole under solvent-free condition and implementation in an industrial scale is economically difficult.

Further, as a process for production of a hydrochloride of an optically active benzyloxypyrrolidine derivative, there is a report that 3 times by mole of 4 M hydrogen chloride-dioxane solution was added to an optically active benzyloxypyrrolidine derivative, and after 2 hours, toluene was added to a concentrated residue to try crystallization (Patent document 3). However, the hydrochloride of an optically active 3-benzyloxypyrroline derivative obtained by this method is described as syrup. As disclosed above, it is difficult to isolate hydrochloride of an optically active 3-benzyloxypyrroline derivative as powder due to very high hygroscopic property.

As described above, there has been found no example of reports on industrial processes of production of a benzyloxypyrrolidine derivative and hydrochloride powder of an optically active benzyloxypyrrolidine derivative, and further, there has been found no example of reports on a hydrochloride powder of an optically active benzyloxypyrrolidine derivative.

Patent document 1: U.S. Pat. No. 5,854,268 Specification (Example 1)
Patent document 2: International Publication 2004-99137 pamphlet (page 142, 2R in EXAMPLE 1)
Patent document 3: U.S. Pat. No. 5,037,841 Specification (Example 49)
Non-patent document 1: Journal of Medicinal Chemistry (42, 4, 685, 1999)

DISCLOSURE OF THE INVENTION

Problem to be Solved by the Invention

Benzyloxypyrrolidine derivatives are useful intermediates; in particular, importance of optically active benzyloxypyrrolidine derivatives as medicine intermediates has been widely recognized. Further, it has been desired that an optically active benzyloxypyrrolidine derivative is highly purified by converting it into hydrochloride. However, in the conventional techniques, there has been no example of reports on production of a benzyloxypyrrolidine derivative in an industrial scale, and further, there has been known that it is difficult to produce hydrochloride of a benzyloxypyrrolidine derivative industrially, in particular, hydrochloride of an optically active benzyloxypyrrolidine derivative. Hence, it has been strongly desired to create an industrial process for production of a benzyloxypyrrolidine derivative in safety and high efficiency, and an industrial process for production of a hydrochloride powder of an optically active benzyloxypyrrolidine derivative.

An object of the present invention is to provide a process for production of a benzyloxypyrrolidine derivative in high yield and safety. Further, another object of the present invention is to provide a process for production of a hydrochloride powder of an optically active benzyloxypyrrolidine derivative, and the process for production in high yield and safety.

Means to Solve the Problem

The present inventors have keenly studied on a process for production of a benzyloxypyrrolidine derivative, and as a result, found out the present invention.

Namely, the present invention is, in reacting a pyrrolidinol derivative represented by the general formula (1) with a benzyl halide derivative in the presence of an alkali metal hydroxide,

[Chemical formula 1]

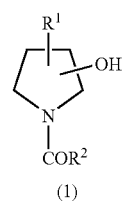

(1)

wherein $R^1$ represents a group selected from i) hydrogen, ii) alkyl group and iii) aryl group; $R^2$ represents a group selected from i) hydrogen, ii) alkoxy group having carbon numbers of from 1 to 4, iii) alkenyloxy group having carbon numbers of from 2 to 4, iv) aralkyloxy group having one benzene ring, v) alkyl group having carbon numbers of from 1 to 4 and vi) aryl group having one benzene ring; and a hydroxyl group may be either 2 or 3 position of pyrrolidine ring;

a process for production of a benzyloxypyrrolidine derivative expressed by the general formula (2), wherein the reaction is carried out in either of the following conditions A or B;
condition A: an aprotic polar solvent,
condition B: an aliphatic ether solvent containing a phase transfer catalyst:

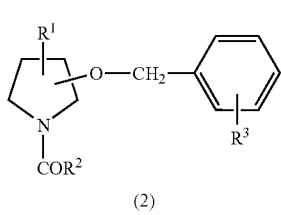

[Chemical formula 2]

(2)

wherein $R^1$ represents a group selected from i) hydrogen, ii) alkyl group and iii) aryl group; and $R^2$ represents a group selected from i) hydrogen, ii) alkoxy group having carbon numbers of from 1 to 4, iii) alkenyloxy group having carbon numbers of from 2 to 4, iv) aralkyloxy group having one benzene ring, v) alkyl group having carbon numbers of from 1 to 4 and vi) aryl group having one benzene ring; $R^3$ represents a group selected from i) hydrogen, ii) alkyl group having carbon numbers of from 1 to 4, iii) alkoxy group having carbon numbers of from 1 to 4 and iv) halogen group.

According to this process, it is possible to produce a benzyloxypyrrolidine derivative in high yield and safety.

The present invention is a process for production of a benzyloxypyrrolidine derivative expressed by the general formula (3), wherein the benzyloxypyrrolidine derivative obtained by said process is treated with an acid substance:

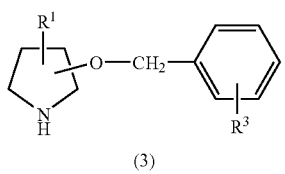

[Chemical formula 3]

(3)

wherein $R^1$ represents a group selected from i) hydrogen, ii) alkyl group and iii) aryl group; and $R^3$ represents a group selected from i) hydrogen, ii) alkyl group having carbon numbers of from 1 to 4, iii) alkoxy group having carbon numbers of from 1 to 4 and iv) halogen group. According to this process, it is possible to eliminate a substituent group on nitrogen efficiently.

As a result of keen studies on a method for obtaining a hydrochloride powder of an optically active benzyloxypyrrolidine derivative by hydrochlorination of an optically active benzyloxypyrrolidine derivative, the present invention is a process for production of a hydrochloride powder of an optically active benzyloxypyrrolidine derivative expressed by the general formula (6), comprising the following two steps:

(a first step) a hydrochlorination step wherein an optically active benzyloxypyrrolidine derivative expressed by the general formula (5) is contacted with hydrogen chloride:

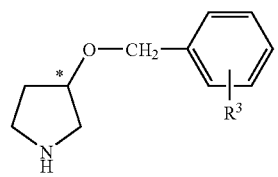

[Chemical formula 4]

(5)

wherein $R^3$ represents a group selected from i) hydrogen, ii) alkyl group having carbon numbers of from 1 to 4, iii) alkoxy group having carbon numbers of from 1 to 4 and iv) halogen group; and * in the formula represents an asymmetric carbon: (a second step) an isolation step where a solution obtained by the first step is crystallized, wherein a molar ratio of hydrogen chloride present in a system is adjusted to from 0.9 to 1.2 based on the optically active benzyloxypyrrolidine derivative by conducting a concentration treatment of said solution or not, then, said solution is fed to crystallization.

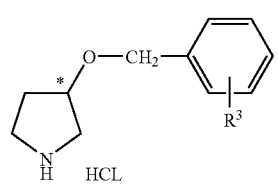

[Chemical formula 5]

(6)

wherein $R^3$ represents a group selected from i) hydrogen, ii) alkyl group having carbon numbers of from 1 to 4, iii) alkoxy group having carbon numbers of from 1 to 4 and iv) halogen group; and * in the formula represents an asymmetric carbon. The hydrochloride powder of an optically active benzyloxypyrrolidine derivative obtained by this process exhibits a property capable of industrial handling, and is clearly different from the conventional known technique.

The present invention is a hydrochloride powder of an optically active benzyloxypyrrolidine expressed by the general formula (7), wherein water absorption when standing still at a relative humidity of 25% and a temperature of 25° C. for 20 hours is 0.5% by weight or less.

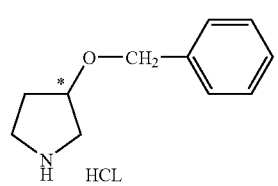

[Chemical formula 6]

(7)

wherein * represents an asymmetric carbon.

EFFECT OF THE INVENTION

According to the present invention, it is possible to produce a benzyloxypyrrolidine derivative using a simple and safe process, and further, it is possible to produce a hydrochloride powder of an optically active benzyloxypyrrolidine derivative capable of industrial handling.

BEST MODE FOR CARRYING OUT THE INVENTION

Hereinafter, the present invention will be described in detail.

The present invention: the general formula (1)

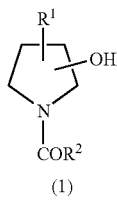

(1)

wherein $R^1$ represents a group selected from i) hydrogen, ii) alkyl group and iii) aryl group; $R^2$ represents a group selected from i) hydrogen, ii) alkoxy group having carbon numbers of from 1 to 4, iii) alkenyloxy group having carbon numbers of from 2 to 4, iv) aralkyloxy group having one benzene ring, v) alkyl group having carbon numbers of from 1 to 4 and vi) aryl group having one benzene ring; and a hydroxyl group may be either 2 or 3 position of pyrrolidine ring;

In reacting a pyrrolidinol derivative represented by the general formula (1) with a benzyl halide derivative in the presence of an alkali metal hydroxide, the present invention is a process for production of a benzyloxypyrrolidine derivative expressed by the general formula (2), wherein the reaction is carried out in either of the following conditions A or B;

condition A: an aprotic polar solvent, condition B: an aliphatic ether solvent containing a phase transfer catalyst:

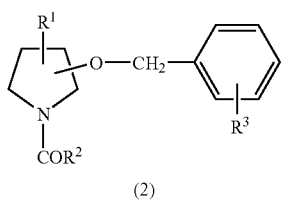

(2)

wherein $R^1$ represents a group selected from i) hydrogen, ii) alkyl group and iii) aryl group; and $R^2$ represents a group selected from i) hydrogen, ii) alkoxy group having carbon numbers of from 1 to 4, iii) alkenyloxy group having carbon numbers of from 2 to 4, iv) aralkyloxy group having one benzene ring, v) alkyl group having carbon numbers of from 1 to 4 and vi) aryl group having one benzene ring; $R^3$ represents a group selected from i) hydrogen, ii) alkyl group having carbon numbers of from 1 to 4, iii) alkoxy group having carbon numbers of from 1 to 4 and iv) halogen group.

In the present invention, a pyrrolidinol derivative represented by the general formula (1) is used:

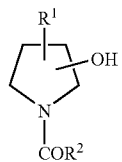

(1)

wherein $R^1$ represents a group selected from i) hydrogen, ii) alkyl group and iii) aryl group; $R^2$ represents a group selected from i) hydrogen, ii) alkoxy group having carbon numbers of from 1 to 4, iii) alkenyloxy group having carbon numbers of from 2 to 4, iv) aralkyloxy group having one benzene ring, v) alkyl group having carbon numbers of from 1 to 4 and vi) aryl group having one benzene ring; and a hydroxyl group may be either 2 or 3 position of pyrrolidine ring; and it may be racemic body or optically active substance. Specific examples can include 1-formyl-2-pyrrolidinol, 1-ethoxycarbonyl-3-pyrrolidinol, 1-tert-butoxycarbonyl-3-pyrrolinol, optically active 1-tert-butoxycarbonyl-3 (S)-pyrrolidinol, optically active 1-tert-butoxycarbonyl-3 (R)-pyrrolidinol-1-allyloxycarbonyl-3-pyrrolidinol, 1-benzyloxycarbonyl-3-pyrrolidinol, 1-acetyl-3-pyrrolidinol, 1-benzyl-3-pyrrolidinol, 1-formyl-3-methyl-2-pyrrolidinol, 1-ethoxycarbonyl-2-n-propyl-3-pyrrolidinol, 1-tert-butoxycarbonyl-2-phenyl-3-pyrrolidinol, 1-allyloxycarbonyl-2-methyl-3-pyrrolidinol, and 1-benzyloxycarbonyl-2-n-butyl-3-pyrrolidinol. Above all, preferable are 1-tert-butoxycarbonyl-3-pyrrolidinol, 1-tert-butoxycarbonyl-2-pyrrolidinol, optically active 1-tert-butoxycarbonyl-3 (S)-pyrrolidinol and optically active 1-tert-butoxycarbonyl-3(R)-pyrrolidinol.

As an alkali metal hydroxide used in the present invention, sodium hydroxide or potassium hydroxide is preferably mentioned. As the alkali metal hydroxide, it may be used as a solid of pellet or flake as it is, or an aqueous solution that is easily handled industrially may be used. In the case of using it as an aqueous solution, the concentration is not particularly limited, but generally, the concentration of alkali metal hydroxide in the aqueous solution is preferably from 10 to 60% by weight, and more preferably from 20 to 50% by weight. The more the used amount of alkali metal hydroxide is, more advantageously the reaction proceeds, but when too much, a problem of operation such as increase in viscosity of reaction liquid is thought. It is preferably from 1 to 10 times by mole based on the pyrrolidinol derivative, more preferably from 2 to 8 times by mole, and further preferably from 2 to 5 times by mole.

The benzyl halide derivative used in the present invention has one benzene ring, and as specific examples, there are listed benzyl chloride, benzyl bromide, 3-chloromethyltoluene, 3-bromomethyltoluene, 4-chloromethyl-3-ethylbenzene, 3-chloromethylanisole, 4-bromomethylanisole, p-chlorobenzyl chloride and the like. Benzyl chloride and benzyl bromide are preferable. The used amount of benzyl halide derivative is from 1 to 2 times by mole based on the pyrrolidinol derivative, preferably from 1 to 1.7 times by mole, and further preferably from 1.1 to 1.5 times by mole. When the used amount is small, it is not good because the conversion rate of pyrrolidinol derivative becomes lowered, whereas when too large, because the amount of by-product of dibenzylated pyrrolidine derivative and dibenzyl ether is increased, thus the above-described suitable range is preferable.

Solvents used in the present invention are an aprotic polar solvent or an aliphatic ether solvent.

As specific examples of the aprotic polar solvent, there are listed dimethylsulfoxide, N,N-dimethylformamide, N,N-dimethylacetamide, formamide, acetamide, N-methyl-2-pyrrolidone and the like, dimethylsulfoxide and N,N-dimethylformamide are preferable. The used amount of the aprotic polar solvent is preferably 1.0 times by weight or more based on the pyrrolidinol derivative, and more preferably 1.3 times by weight or more. A reaction system in the present invention may be a uniform system or slurry, but when less than 1.0 times by mass, it becomes more concentrated reaction liquid, so that operability of stirring tends to be deteriorated. Further, the larger the used amount of the aprotic polar solvent is, the better the stirring condition is, but being too much invites an increase in the used amount of solvent and the lowering of productivity, thus 10 times by weight or less is preferable, and 3.0 times by weight or less is more preferable from the point of suppressing the used amount of solvent as much as possible.

On the other hand, in the case of an aliphatic ether solvent, it is essential to use a phase transfer catalyst. As specific examples of the aliphatic ether solvent, there can be listed tetrahydrofuran, tetrahydropirane, isopropyl ether, cyclopentyl methyl ether, diethyl ether, dimethoxyethane and the like, tetrahydrofuran is preferable. The used amount of the aliphatic ether solvent is preferably 1.0 times by weight or more based on the pyrrolidinol derivative, but being too much invites an increase in the used amount of solvent and the lowering of productivity, thus 10 times by weight or less is preferable, and 3.0 times by weight or less is more preferable from the point of suppressing the used amount of solvent as much as possible.

Further, the coexistent phase transfer catalyst is not particularly limited, quaternary ammonium salt or quaternary phosphonium salt is mentioned. Preferably, it is a quaternary ammonium salt expressed by the general formula (8):

[Chemical formula 10]

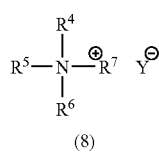

(8)

wherein $R^4$ to $R^7$ represent the same or different alkyl group having carbon numbers of from 1 to 18, or a benzyl group, Y represents a halogen atom, a sulfuric acid ion, or a hydroxide ion. As the specific examples, there are preferably listed tetra-n-butylammonium bromide, tetra-n-butylammonium chloride, n-dodecyltrimethylammonium chloride, n-dodecyltrimethylammonium bromide, tetraethylammonium bromide, benzyltri-n-butylammonium chloride, benzyltrimethylammonium chloride, tetra-n-butylammonim sulfate, di-n-dodecyldimethylammonium chloride and the like; further preferable are tetra-n-butylammonium bromide, n-dodecyltrimethylammonium bromide and tetra-n-butylammonim sulfate. The used amount of the phase transfer catalyst is from 0.001 to 0.5 times by mole based on the pyrrolidinol derivative, preferably from 0.005 to 0.3 times by mole, and further preferably from 0.01 to 0.10 times by mole. In this range, it is possible to convert a pyrrolidinol derivative efficiently into a corresponding benzyloxypyrrolidine derivative.

Further, in either an aprotic polar solvent or an aliphatic ether solvent, it may be a mixed solvent of water and thereof. The ratio of water in the solvent is not particularly limited, it is preferably from 1 to 80% by weight, and further preferably from 10 to 50% by weight.

Regarding the reaction method, it is suitable to add a benzyl halide derivative after mixing of a pyrrolidinol derivative, a solvent and an alkali metal hydroxide, and in the case of an aliphatic ether solvent, further adding a phase-transfer solvent, in order to exhibit a maximum effect of the present invention. When an alkali metal hydroxide and water first contact a benzyl halide derivative, there is a tendency that benzyl alcohol or dibenzyl ether corresponding to a benzyl halide derivative generates in a large amount as by-product. The temperature that a benzyl halide derivative is added dropwise and the aging temperature are from 0 to 100° C., preferably from 0 to 70° C., and further preferably from 0 to 50° C.

The thus obtained benzyloxypyrrolidine derivative is expressed by the general formula (2):

[Chemical formula 11]

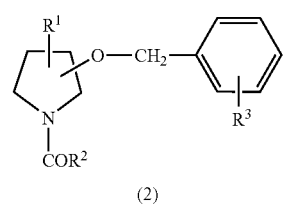

(2)

wherein $R^1$ represents a group selected from i) hydrogen, ii) alkyl group and iii) aryl group; and $R^2$ represents a group selected from i) hydrogen, ii) alkoxy group having carbon numbers of from 1 to 4, iii) alkenyloxy group having carbon numbers of from 2 to 4, iv) aralkyloxy group having one benzene ring, v) alkyl group having carbon numbers of from 1 to 4 and vi) aryl group having one benzene ring; $R^3$ represents a group selected from i) hydrogen, ii) alkyl group having carbon numbers of from 1 to 4, iii) alkoxy group having carbon numbers of from 1 to 4 and iv) halogen group. As the specific example, there are listed 1-tert-butoxycarbonyl-3-benzyloxypyrrolidine, 1-tert-butoxycarbonyl-2-methyl-3-benzyloxypyrrolidine, 1-tert-butoxycarbonyl-4-methyl-3-benzyloxypyrrolidine, 1-tert-butoxycarbonyl-4-phenyl-3-benzyloxypyrrolidine, 1-tert-butoxycarbonyl-5-phenyl-3-benzyloxypyrrblidine, 1-tert-butoxycarbonyl-2-n-butyl-3-benzyloxypyrrolidine, 1-tert-butoxycarbonyl-4-n-butyl-3-benzyloxypyrrolidine, 1-tert-butoxycarbonyl-5-n-butyl-3-benzyloxypyrrolidine, 1-ethoxycarbonyl-2-methyl-3-benzyloxypyrrolidene, 1-ethoxycarbonyl-4-methyl-3-benzyloxypyrrolidene, 1-ethoxycarbonyl-5-methyl-3-benzyloxypyrrolidene, 1-ethoxycarbonyl-2-ethyl-3-benzyloxypyrrolidene, 1-ethoxycarbonyl-4-ethyl-3-benzyloxypyrrolidene, 1-ethoxycarbonyl-5-ethyl-3-benzyloxypyrrolidene, 1-ethoxycarbonyl-3-benzyloxypyrrolidine and the like, 1-tert-butoxycarbonyl-3-benzyloxypyrrolidine is preferable, and it may be a racemic body or an optically active substance.

Next, by treating the benzyloxypyrrolidine derivative obtained by the above methods with an acid substance, it is possible to produce a benzyloxypyrrolidine derivative expressed by the general formula (3):

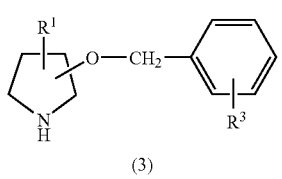

(3)

wherein $R^1$ represents a group selected from i) hydrogen, ii) alkyl group and iii) aryl group; and $R^3$ represents a group selected from i) hydrogen, ii) alkyl group having carbon numbers of from 1 to 4, iii) alkoxy group having carbon numbers of from 1 to 4 and iv) halogen group.

As an acid substance used here, there can be listed mineral acids such as hydrochloric acid and sulfuric acid, and carboxylic acids such as formic acid, acetic acid, monochloroacetic acid, dichloroacetic acid, trichloroacetic acid and propionic acid. Above all, hydrochloric acid and sulfuric acid are preferably listed. The used amount of the acid substance is, from consideration of the amount of base present in benzylation reaction, from 0.1 to 10 times by mole based on the benzyloxypyrrolidine derivative, preferably from 0.5 to 5 times by mole, and further preferably from 1 to 5 times by mole. The treatment temperature using an acid substance is ordinarily from 0 to 100° C., preferably from 10 to 70° C., and further preferably from 20 to 60° C. Further, without isolating a benzyloxypyrrolidine derivative from the reaction liquid containing the benzyloxypyrrolidine derivative obtained by the above-described methods, even by adding the above-described acid substance, the reaction proceeds efficiently, which leads to a process with easy operation and good efficiency. After the resulting benzyloxypyrrolidine derivative is subjected to an acid treatment, it becomes acid salt, and can be purified by being washed with an organic solvent such as toluene, and further, alkalified and extracted with an organic solvent such as toluene, thereby to isolate a benzyloxypyrrolidine derivative. It is possible to obtain a benzyloxypyrrolidine derivative with high purity by distillation or crystallization after concentrating the toluene layer.

As specific examples of the benzyloxypyrrolidine derivative thus obtained, there are listed 3-benzyloxypyrrolidine, 2-benzyloxypyrrolidine, 2-methyl-3-benzyloxypyrrolidine, 4-methyl-3-benzyloxypyrrolidine, 5-methyl-3-benzyloxypyrrolidine, 2-ethyl-3-benzyloxypyrrolidine, 4-ethyl-3-benzyloxypyrrolidine, 5-ethyl-3-benzyloxypyrrolidine, 2-phenyl-3-benzyloxypyrrolidine, 4-phenyl-3-benzyloxypyrrolidine, 5-phenyl-3-benzyloxypyrrolidine, 2-n-butyl-3-benzyloxypyrrolidine, 4-n-butyl-3-benzyloxypyrrolidine, 5-n-butyl-3-benzyloxypyrrolidine, 2-methyl-3-benzyloxypyrrolidine, 4-methyl-3-benzyloxypyrrolidine, 5-methyl-3-benzyloxypyrrolidine, 2-ethyl-3-benzyloxypyrrolidine, 4-ethyl-3-benzyloxypyrrolidine, 4-ethyl-3-benzyloxypyrrolidine, 5-ethyl-3-benzyloxypyrrolidine, 2-phenyl-3-benzyloxypyrrolidine, 4-phenyl-3-benzyloxypyrrolidine, 5-phenyl-3-benzyloxypyrrolidine, 2-n-butyl-3-benzyloxypyrrolidine, 4-n-butyl-3-benzyloxypyrrolidine, 5-n-butyl-3-benzyloxypyrrolidine, and the like, and preferably, it is a benzyloxypyrrolidine derivative expressed by the general formula 3':

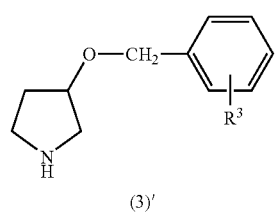

(3)' wherein $R^3$ represents a group selected from i) hydrogen, ii) alkyl group having carbon numbers of from 1 to 4, iii) alkoxy group having carbon numbers of from 1 to 4 and iv) halogen group. As a specific example, there are listed 3-benzyloxypyrrolidine expressed by the following formula (4):

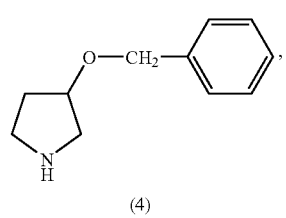

(4)

Optically active 3(S)-benzyloxypyrrolidine, optically active 3(R)-benzyloxypyrrolidine, 3-(3-methylbenzyloxy)pyrrolidine, 3-(2-ethoxybenzyloxy)pyrrolidine and 3-(4-chlorobenzyloxy)pyrrolidine, and preferable are 3-benzyloxypyrrolidine, optically active 3(S)-benzyloxypyrrolidine and optically active 3(R)-benzyloxypyrrolidine.

These benzyloxypyrrolidine derivatives can be converted into a hydrochloride powder of an optically active benzyloxypyrrolidine derivative expressed by the following formula (6) by the following steps: (first step); a hydrochlorination step contacting hydrogen chloride with an optically active benzyloxypyrrolidine derivative expressed by general formula (5):

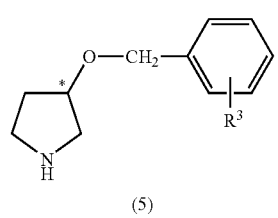

(5)

wherein $R^3$ represents a group selected from i) hydrogen, ii) alkyl group having carbon numbers of from 1 to 4, iii) alkoxy group having carbon numbers of from 1 to 4 and iv) halogen group; and * in the formula represents an asymmetric carbon: (a second step) an isolation step where a solution obtained by the first step is crystallized, wherein a molar ratio of hydrogen chloride present in a system is adjusted to from 0.9 to 1.2 based on the optically active benzyloxypyrrolidine derivative by conducting a concentration treatment of said solution or not, then, said solution is fed to crystallization.

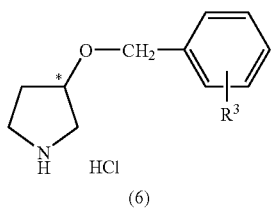

[Chemical formula 16]

(6)

wherein R³ represents a group selected from i) hydrogen, ii) alkyl group having carbon numbers of from 1 to 4, iii) alkoxy group having carbon numbers of from 1 to 4 and iv) halogen group; and * in the formula represents an asymmetric carbon.

Hydrogen chloride used in the first step is preferably hydrogen chloride previously dissolved in an organic solvent (for example, hydrogen chloride dissolved in an organic solvent by contacting hydrogen chloride gas with an organic solvent), and specifically, it can be obtained by blowing hydrogen chloride gas into an organic solvent (in this case, an organic solvent that hydrogen chloride is dissolved is prepared by contacting hydrogen chloride gas with an organic solvent beforehand, which is contacted with an optically active benzyloxypyrrolidine derivative, leading to contact of an optically active benzyloxypyrrolidine derivative and hydrogen chloride). In addition, hydrogen chloride that an aqueous hydrogen chloride solution typified by concentrated hydrochloric acid is contacted with an organic solvent may be used. In this case, generally, it is necessary to undergo a concentration step, and as a result, there is a tendency that colored powders are obtained. Therefore, the former method excels in the case where color becomes problems. The concentration of hydrogen chloride in the organic solvent thus obtained can be determined by neutralization titration. The concentration of hydrogen chloride in an organic solvent is not particularly limited, but generally, it is preferably in a range of from 1 to 20% by weight, more preferably from 1 to 15% by weight, and preferably saturated solubility or lower.

The organic solvent used in the first step (hereinafter, referred to as hydrochlorination solvent) is not particularly limited, and when it is the same as the organic solvent used in the second step (hereinafter, referred to as crystallization solvent), it is efficient because operations such as solvent substitution can be skipped. On the other hand, when a hydrochlorination solvent is different from a crystallization solvent, generally, solvent substitution can be done by a method such as concentration.

Further, when the used amount of hydrogen chloride is from 0.9 to 1.2 times by mole based on the benzyloxypyrrolidine derivative, no concentration treatment is required in the second step, operation becomes simple and efficient. When less than 0.9, it becomes disadvantageous because the production amount of hydrochloride of an optically active benzyloxypyrrolidine derivative is lowered, and when more than 1.2, a hydrochloride powder of an optically active benzyloxypyrrolidine derivative can be obtained if excess hydrogen chloride in hydrochloride formation of an optically active benzyloxypyrrolidine derivative in the second step is concentrated and removed.

As specific examples of the hydrochlorination solvent of an optically active benzyloxypyrrolidine derivative, there can be listed ethers such as tetrahydrofuran, tetrahydropyran, 1,4-dioxane, 1,3-dioxane, diisopropyl ether, dibutyl ether, cyclopentyl methyl ether and anisole; alcohols such as methanol, ethanol, 1-propanol, 2-propanol, 1-butanol, 2-butanol and isobutyl alcohol; and nitriles such as acetonitrile, propionitrile and butyronitrile, ether is preferable, more preferable are tetrahydrofuran, 1,4-dioxane, diisopropyl ether and cyclopentyl methyl ether, further preferable are aliphatic ethers such as tetrahydrofuran and diisopropyl ether.

Although the operation method in the first step is not particularly limited, a specific method will be exemplified. A most preferable method is a method that an optically active benzyloxypyrrolidine derivative or an organic solvent solution thereof is added dropwise to an organic solvent that hydrochloride is dissolved under from ice cooling to room temperature. According to this method, speed control of hydrochlorination is easy and it is advantageous from the point of temperature control. Reversely, it is also possible that an organic solvent that hydrogen chloride is dissolved is added dropwise to a benzyloxypyrrolidine derivative or an organic solvent solution thereof. Temperature increases due to heat of neutralization is observed in either of them, and in the case of extreme local heat generation or insufficient cooling in dropping, hydrochlorination solution colors sometimes; thus, when suppression of coloring is wanted, the temperature control is important, the temperature is preferably from 0 to 20° C. and more preferably from 0 to 10° C.

Further, hydrochlorination can be done in such manner that a concentrated hydrochloric aqueous solution (about 35% by weight) is added dropwise to an optically active benzyloxypyrrolidine derivative or an organic solvent solution thereof. After mixing both, hydrochlorination is accelerated by stirring, but generally, it is thought that hydrochlorination is completed just by mixing. After mixing, it is aged till the reaction of hydrochlorination is completed, and the aging temperature is preferably from ice cooling to room temperature; above all, from 0 to 30° C. is more preferable. The aging time is generally from 10 minutes to 12 hours, and preferably from 30 minutes to 2 hours. The thus obtained hydrochloride solution is used in the second step without modification.

The second step aims to isolate the hydrochloride obtained in the first step. In the present step, the used amount of hydrogen chloride in the hydrochloride solution obtained in the first step needs to be adjusted to from 0.9 to 1.2 times by mole based on the optically active benzyloxypyrrolidine derivative. For example, when the used amount of hydrogen chloride in the first step is from 0.9 to 1.2 times by mole based on the optically active benzyloxypyrrolidine derivative, in the present step, it is possible to carry out crystallization without conducting a concentration treatment, thereby to obtain a hydrochloride powder of an optically active benzyloxypyrrolidine derivative in good yield. Additionally, as long as the amount of hydrogen chloride in the hydrochloride solution to be fed to crystallization is in the above-described range, treatments such as concentration and dilution may be conducted, which only increases steps and provides little merit. Further, powders obtained by concentration tend to color.

On the other hand, when the used amount of hydrogen chloride in the first step is more than 1.2 times by mole based on the optically active benzyloxypyrrolidine derivative, after excess hydrogen chloride in hydrochloride formation is removed by the concentration treatment, and the molar ratio is adjusted to from 1.0 to 1.2 (because equimolar hydrogen chloride is used for forming hydrochloride, generally, it does not become less than 1.0 in concentration), crystallization is carried out, thereby a hydrochloride powder of an optically active benzyloxypyrrolidine derivative can be obtained in good yield.

However, colored powders are easily obtained; hence, it is preferable to control a molar ratio of hydrogen chloride to an optically active benzyloxypyrrolidine derivative in the above-described range without undergoing a concentration step. Further, by controlling the molar ratio in from 0.9 to 1.2 times by mole, a powder having further smaller water absorption can be obtained in high yield. It is preferable that the concentration treatment is done under reduced pressure just capable of distilling a solvent away and in a condition of as low temperature as possible from the points of prevention of color due to thermal history and prevention of impurities.

The content of hydrogen chloride can be determined by carrying out a silver nitrate-titration analysis of the liquid subjected to a concentration treatment, and separately, the molar ratio can be calculated by carrying out a quantitative analysis of an optically active benzyloxypyrrolidine derivative. This quantitative analysis can also be applied to a solution not subjected to the concentration treatment. In any way, adjustment of the molar ratio is very important, and when the molar ratio of the used amount of hydrogen chloride in a system of a solution to be fed to crystallization is more than 1.2, it is thought that hydrochloride tends to be a supersaturated state due to excess hydrogen chloride, and precipitation of powder is extremely disturbed.

The crystallization solvent used in the second step may use various ones, and as the specific examples, there can be listed hydrocarbons such as benzene, toluene, o-xylene, m-xylene, p-xylene, 1,3,5-trimethylbenzene, n-hexane and n-heptane; ethers such as tetrahydrofuran, tetrahydropyran, 1,4-dioxane, 1,3-dioxane, diisopropyl ether, dibutyl ether, cyclopentyl methyl ether and anisole; alcohols such as methanol, ethanol, 1-propanol, 2-propanol, 1-butanol, 2-butanol, isobutyl alcohol; and nitriles such as acetonitrile, propionitrile and butyronitrile. Preferable is at least one kind of solvent selected from hydrocarbons and ethers, and more preferable is at least one kind of solvent selected from hydrocarbons such as an aromatic hydrocarbon and aliphatic ethers, and a mixed solvent thereof is preferably used. For example, a mixed solvent of tetrahydrofuran and toluene is particularly preferably mentioned from the point of remarkable effects of the present invention, the composition ratio depends on the kind of an optically active benzyloxypyrrolidine derivative, and generally, the content of tetrahydrofuran is preferably in a range of from 1 to 99% by weight, more preferably in a range of from 5 to 95% by weight, and further preferably in a range of from 10 to 90% by weight. The larger the content of tetrahydrofuran is, the better quality the product has. Namely, an aromatic hydrocarbon is a poor solvent for an optically active benzyloxypyrrolidine derivative and an aliphatic ether is a good solvent for an optically active benzyloxypyrrolidine derivative, and thus, a mixed solvent of both is effective to obtain a hydrochloride powder of an optically active benzyloxypyrrolidine derivative in good quality.

As described above, as the specific example of a hydrochloride powder of an optically active benzyloxypyrrolidine derivative expressed by the general formula (6) obtained by contacting an optically active benzyloxypyrrolidine derivative with hydrogen chloride in an organic solvent:

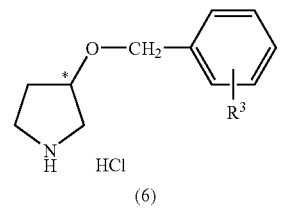

[Chemical formula 17]

(6)

(wherein $R^3$ represents a group selected from i) hydrogen, ii) alkyl group having carbon numbers of from 1 to 4, iii) alkoxy group having carbon numbers of from 1 to 4 and iv) halogen group; and * in the formula represents an asymmetric carbon.), there can be listed 3(S)-benzyloxypyrrolidine hydrochloride, 3(R)-benzyloxypyrrolidine hydrochloride, 3(S)-o-methylphenylmethoxypyrrolidine hydrochloride, 3(R)-o-methylphenylmethoxypyrrolidine hydrochloride, 3(S)-m-methylphenylmethoxypyrrolidine hydrochloride, 3(R)-m-methylphenylmethoxypyrrolidine hydrochloride, 3(S)-p-methylphenylmethoxypyrrolidine hydrochloride, 3(R)-p-methylphenylmethoxypyrrolidine hydrochloride, 3(S)-p-ethylphenylmethoxypyrrolidine hydrochloride, 3(S)-p-isopropylphenylmethoxypyrrolidine hydrochloride, 3(R)-p-n-butylphenylmethoxypyrrolidine hydrochloride, 3(R)-p-tert-butylphenylmethoxypyrrolidine hydrochloride, 3(S)-o-methoxyphenylmethoxypyrrolidine hydrochloride, 3(R)-m-methoxyphenylmethoxypyrrolidine hydrochloride, 3(R)-p-methoxyphenylmethoxypyrrolidine hydrochloride, 3(S)-p-ethoxyphenylmethoxypyrrolidine hydrochloride, 3(R)-p-isopropoxyphenylmethoxypyrrolidine hydrochloride, 3(S)-p-tert-butoxypyrrolidine hydrochloride, 3(R)-o-chlorophenylmethoxypyrrolidine hydrochloride, 3(R)-m-bromophenylmethoxypyrrolidine hydrochloride, 3(S)-p-iodophenylmethoxypyrrolidine hydrochloride and the like, and preferably, an optically active benzyloxypyrrolidine hydrochloride expressed by the general formula (7):

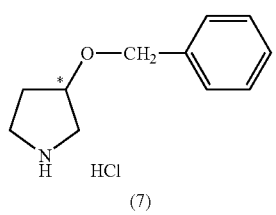

[Chemical formula 18]

(7)

Specifically, 3(S)-benzyloxypyrrolidine hydrochloride and 3(R)-benzyloxypyrrolidine hydrochloride Regarding the method of crystallization, when to a solution that a molar ratio of hydrogen chloride and an optically active benzyloxypyrrolidine derivative is adjusted to from 0.9 to 1.2, a seed crystal is added and aged, it is possible to crystallize nicely without scaling. In this case, a solution before crystallization may be a homogeneous solution, or may be separated into two liquid-liquid phases. However, in the case where crystals have already precipitated before adding a seed crystal, addition of seed crystal is not required. The temperature of crystallization which is carried out is generally from −20 to room temperature, preferably from −5 to 20° C., and more preferably from ice cooling to 10° C. Further, to isolate the precipitated hydrochloride powder of an optically active benzyloxypyrrolidine derivative, it can be done by ordinary methods such as filtration and centrifugal separation. The powder shows deliquescence or high hygroscopic property, so that the operations are all conducted generally under an inert gas atmosphere.

Further, regarding hydrochloride of an optically active benzyloxypyrrolidine derivative, water is generally used in its synthesis process, and water is generally contained in a solution to be fed for crystallization. In precipitating hydrochloride in the second step, it has been found that moisture content in the system influences a hydrochloride powder of an optically active benzyloxypyrrolidine derivative on yield, operability and quality (appearance, moisture absorption property, purity). Namely, it is preferable that moisture content in a system is 0.1 times by mole or less based on the optically active benzyloxypyrrolidine derivative. Quality and appearance of the resulting hydrochloride powder of an optically active benzyloxypyrrolidine derivative are greatly influenced by water in a system in the crystallization step, and thus, it is particularly preferable that moisture content is 0.05 times by mole or less based on the optically active benzyloxypyrrolidine derivative. In the present invention, containing no water is most preferable. Therefore, the lower limit of the preferable moisture content is 0 times by mole. In the present invention, by setting moisture content in the above-described range, it is possible to obtain a powder with high purity and good yield.

In the present invention, when water is excessively present in a system, it is difficult for hydrochloride of an optically active benzyloxypyrrolidine derivative to become powder, and, even when ground into powder, it has viscosity and tends to form a block; therefore, it becomes difficult to take out crystal due to blocking after filtration and drying, and product purity is lowered due to lots of impurities because the crystal contains much of mother liquid.

The precipitated hydrochloride of an optically active benzyloxypyrrolidine derivative can be recovered by a method such as filtration, washed with a suitable solvent and dried to separate it as powder. As a method for drying the obtained hydrochloride powder of an optically active benzyloxypyrrolidine derivative, drying in vacuum may be done, but drying under reduced pressure in a stream of inert gas such as nitrogen is common. The hydrochloride of an optically active benzyloxypyrrolidine derivative obtained as described above is generally of a powder form, and the optically active benzyloxypyrrolidine derivative produced in a preferable mode can be obtained as a powder with low water absorption in such manner that its water absorption is 0.5% by weight or less when standing still at a relative humidity of 25% and a temperature of 25° C. for 20 hours; when it is produced in more preferable mode, there can be obtained one with 0.3% by weight or less; when it is produced in further preferable mode, there can be obtained one with 0.2% by weight or less. The measurement of water absorption is carried out in the following method.

Since a hydrochloride powder of an optically active benzyloxypyrrolidine derivative is generally deliquescent, it is dewatered once in vacuum drying before a water absorption experiment. Generally, pretreatment of a sample for a water absorption experiment is carried out in such manner that a sample of about 1 g is dried at 20±10 Torr, 45±5° C. for 5 hours, and the sample weight is precisely weighed before and after water absorption treatment. The water absorption of hydrochloride powder of an optically active benzyloxypyrrolidine derivative can be calculated by the following formula.

Water absorption (%)={(sample weight after water absorption treatment−sample weight before water absorption treatment)/(sample weight before water absorption treatment)}×100 (wt %)

The water absorption experiment can be carried out by using a commercially available constant temperature constant humidity apparatus. Inside of a container used in the water absorption experiment may be monitored full-time by a thermohygrometer. Relative humidity 25% and temperature 25° C. in the present invention represent 25±1% and 25±1° C., respectively.

By the methods described above, a hydrochloride powder of an optically active benzyloxypyrrolidine derivative with high purity can be obtained in high yield and good repeatability.

The hydrochloride of a benzyloxypyrrolidine derivative thus obtained can be handled even in the case of production in an industrial scale.

EXAMPLES

Hereinafter, the present invention will be described further in detail with reference to Examples, but the present invention is not limited thereto.

Herein, there will be explained a method that an optically active 1(R)-benzyloxy-1-tert-butoxycarbonylpyrrolidine (hereinafter, called R-BocBHP) is synthesized from an optically active 1-tert-butoxycarbonyl-3(R)-hydroxypyrrolidine (hereinafter, called R-BocHP) by benzyl chloride.

Reaction yield was calculated by analysis using HPLC set in the following conditions. A reaction liquid was analyzed in a state of reaction liquid without isolating a product using an internal standard method. Further, an optically active 3(R)-benzyloxypyrrolidine (hereinafter, called R-3BHP) obtained by deprotection (de-Boc) of R-BocBHP was also quantitatively determined in a state of reaction liquid without modification in the same analysis conditions.

Column: RP-18 C18, 4.6 mm×150 mm (Kanto Chemical Co., Inc.)

Moving phase: 5 mM sodium dodecylsulfate aqueous solution (adjusted to pH 2.5 with phosphoric acid)/$CH_3CN$=70/30 (0-30 min.) to 30/70 (30-45 min.)

Flow rate: 1.0 ml/min

Temperature: 40° C.

Detector: UV (210 nm)

Further, optical purity of R-BocBHP can be obtained in such manner that after the Boc group is deprotected to change into R-3BHP, which is treated with O,O'-di-p-toluoyl-L-tartaric acid anhydride to be converted into diastereomer of an optically active tartaric acid derivative, which is subjected to HPLC analysis. HPLC analysis conditions are written as follows.

Column: CAPCELLPAK C18, SG120, S-5 μm, 4.6 mmφ×250 mm (Shiseido Co., Ltd.)

Moving phase: 0.03% ammonia water (pH 4.5; adjusted with acetic acid)/methanol=41/59 (v/v)

Flow rate: 1.0 ml/min

Detector: UV 234 nm

Temperature: 40° C.

Reference Example 1

Synthesis of optically active R-BocHP used in the present invention is as follows.

To a 2 L flask equipped with a Dienstark dehydration apparatus, 209.6 g (0.160 moles) of (4R)-hydroxy-L-proline (Tokyo Chemical Industry Co., Ltd.; highest quality) and 800 g (8.16 moles) of cyclohexanone (Katayama Chemical Industries Co., Ltd., first quality) were added, and heat refluxed at a temperature in the range from 150 to 160° C. while conducting azeotropic dehydration. After 1 hour, it was confirmed that crystal disappeared and became a homogeneous solution, and the solution was cooled to room temperature. Water of 800 ml was added thereto and stirred for 1 hour, an aqueous layer was concentrated, then distilled under reduced pressure to obtain 114.4 g (1.31 moles) of 3(R)-hydroxypyrrolidine (R—HP) as a fraction of from 110 to 115° C./1.3 to 1.7 kPa (isolation yield: 83%, optical purity: 99.9% ee. or more).

Next, in a four-neck flask of 500 ml equipped with a thermometer and a dropping funnel, 65.1 g (0.75 moles) of the R—HP obtained above was charged, and 130.3 g of methanol was added thereto and ice-cooled. To this solution, 171.4 g (0.79 moles) of di-tert-butyl dicarbonate was added dropwise while maintaining the liquid temperature at 20° C. or less. After completion of dropping, the resulting mixture was aged for 1 hour, concentrated, and about 200 g was distilled away. To this concentrated liquid, 250 g of n-heptane was added and stirred, and cooled at a temperature in the range from 15 to 20° C., followed by stirring overnight. Slurry was subjected to solid-liquid separation, 152.9 g of crystal was collected by filtration, and dried in vacuum, thereby to obtain R-BocHP of 122.5 g (isolation yield: 87%).

(Production of R-BocBHP)

A method for synthesis of R-BocBHP by reacting The R-BocHP obtained above with benzyl chloride will be described below.

(Reaction Using Aprotic Polar Solvent)

Example 1

In a four-neck flask of 1 L equipped with a thermometer and a dropping funnel, 182.0 g of dimethylsulfoxide was charged, 121.3 g (0.65 moles) of R-BocHP obtained above was added thereto and stirred to dissolve. Next, 48% sodium hydroxide of 162.0 g (1.94 moles) (3.0 equivalent amount to R-BocHP) was added, and while stirring, benzyl chloride of 106.6 g (0.84 moles) (1.3 equivalent amount to R-BocHP) was added dropwise for the inner temperature to be from 30 to 40° C. in a water bath. After aging of 7 hours, the reaction liquid was quantitatively analyzed using the above-described HPLC analysis method, as a result, the production amount of R-BocBHP was 171 g (reaction yield: 95%).

Next, while maintaining the inner temperature at a temperature in the range from 45 to 55° C., 283.4 g (2.72 moles) of concentrated hydrochloric acid was added dropwise, and aged for 3 hours at the same temperature. This reaction liquid was analyzed using the above-described HPLC analysis method, and as a result, the production amount of R-3BHP was 106.2 g (de-Boc yield: 97%). After this reaction liquid was washed with toluene, it was alkalized with 48% sodium hydroxide, and extracted with toluene. The mixture was concentrated, then distilled under reduced pressure to obtain 95.9 g of a fraction of 120° C. (0.93 kPa) (recovery rate: 90%).

The optical purity of the R-3BHP obtained was 99.9% ee. or more.

The following study was carried out by reducing the reaction scale of Example 1 by 1/10.

Examples 2 to 4

Form of NaOH

In Example 1, the used amount of each component was set to the following and the form of sodium hydroxide was changed variously for doing studies and the results are shown in Table 1. In the table, the used amount of solvent represents times by weight based on R-BocHP.

TABLE 1

| | Solvent | | Benzylation agent | | Base | | Reaction yield (%) |
|---|---|---|---|---|---|---|---|
| | Kind | Used amount | Kind | Equivalent number | Kind | Equivalent number | |
| Example-2 | DMSO | 6 | BnCl | 1.1 | 48% NaOH aqueous solution | 5 | 93.0 |
| Example-3 | DMSO | 6 | BnCl | 1.1 | NaOH pellet | 5 | 97.7 |
| Example-4 | DMSO | 6 | BnCl | 1.1 | NaOH flake | 5 | 96.0 |

From the above table, it is known that sodium hydroxide may be used either in the form of aqueous solution or solid.

Examples 5 to 7

Used Amount of NaOH

In Example 1, the used amount of 48% sodium hydroxide aqueous solution (hereinafter, sometimes abbreviated as "48% NaOH") was variously changed for doing studies and the results are shown in Table 2.

TABLE 2

| | Solvent | | Benzylation agent | | Base | | |
|---|---|---|---|---|---|---|---|
| | Kind | Used amount | Kind | Equivalent number | Kind | Equivalent number | Reaction yield (%) |
| (Example-2) | DMSO | 6 | BnCl | 1.1 | 48% NaOH | 5 | 93.0 |
| Example-5 | DMSO | 6 | BnCl | 1.2 | 48% NaOH | 3 | 92.8 |
| Example-6 | DMSO | 6 | BnCl | 1.2 | 48% NaOH | 2 | 91.4 |
| Example-7 | DMSO | 6 | BnCl | 1.2 | 48% NaOH | 1 | 89.1 |

From the above table, to progress the reaction efficiently, the more the used amount of base is, the better.

Examples 8 to 10

Used Amount of Benzyl Chloride

In Example 1, the used amount of benzyl chloride was variously changed for doing studies and the results are shown in Table 3.

TABLE 3

| | Solvent | | Benzylation agent | | Base | | |
|---|---|---|---|---|---|---|---|
| | Kind | Used amount | Kind | Equivalent number | Kind | Equivalent number | Reaction yield (%) |
| Example-8 | DMSO | 3 | BnCl | 1.1 | 48% NaOH | 3 | 91.8 |
| Example-9 | DMSO | 3 | BnCl | 1.2 | 48% NaOH | 3 | 97.1 |
| Example-10 | DMSO | 3 | BnCl | 1.3 | 48% NaOH | 3 | Quantitatively |

From the above table, to progress the reaction efficiently, the more the used amount of benzyl chloride is, the better. In the table, being quantitatively means that the calculated result based on analytical results by a predetermined HPLC analysis was 99% or more.

Examples 11 to 14

Used Amount of DMSO

In Example 1, the used amount of solvent was changed for doing studies of benzylation reaction and the results are shown in Table 4.

TABLE 4

| | Solvent | | Benzylation agent | | Base | | |
|---|---|---|---|---|---|---|---|
| | Kind | Used amount | Kind | Equivalent number | Kind | Equivalent number | Reaction yield (%) |
| Example-11 | DMSO | 1.0 | BnCl | 1.3 | 48% NaOH | 3 | 93.6 |
| Example-12 | DMSO | 1.3 | BnCl | 1.3 | 48% NaOH | 3 | Quantitatively |
| Example-13 | DMSO | 1.7 | BnCl | 1.3 | 48% NaOH | 3 | Quantitatively |
| Example-14 | DMSO | 2.0 | BnCl | 1.3 | 48% NaOH | 3 | Quantitatively |

From the above table, to progress the reaction efficiently, it is particularly good that the used amount of dimethylsulfoxide (DMSO) is 1.3 times by weight or more based on R-BocHP.

Examples 15 to 18

Reaction Temperature

In Example 1, the reaction temperature was changed for doing studies of benzylation reaction and the results are shown in Table 5.

TABLE 5

| | Solvent | | Benzylation agent | | Base | | Reaction temperature (° C.) | Reaction yield (%) |
|---|---|---|---|---|---|---|---|---|
| | Kind | Used amount | Kind | Equivalent number | Kind | Equivalent number | | |
| Example-15 | DMSO | 3.0 | BnCl | 1.2 | 48% NaOH | 3 | 20 | 86.7 |
| Example-16 | DMSO | 3.0 | BnCl | 1.2 | 48% NaOH | 3 | 30 | Quantitatively |
| Example-17 | DMSO | 3.0 | BnCl | 1.2 | 48% NaOH | 3 | 50 | 96.8 |
| Example-18 | DMSO | 3.0 | BnCl | 1.2 | 48% NaOH | 3 | 70 | 91.5 |

From the above table, to progress the reaction efficiently, it is particularly good that the reaction temperature is from 30 to 70° C.

Example 19

Comparative Examples 1 to 8

In Example 1, the solvent was variously changed for doing studies and the results are shown in Table 6.

Additionally, there were used pellet for KOH and powder for sodium methylate.

(Reaction Using Aliphatic Ether Solvent Containing Phase Transfer Catalyst)

Similarly, a method that R-BocBHP is synthesized by reacting R-BocHP with benzyl chloride will be described below.

Example 20

In a 50 mL flask equipped with a thermometer and a dropping funnel, to a mixed liquid of R-BocHP of 1.01 g (5.39 mmol), tetrahydrofuran of 1.50 g, tetra-n-butylammonium bromide of 90.3 mg (0.28 mmol, 0.05 equivalent amount to R-BocHP) and 48% sodium hydroxide aqueous solution of 1.37 g (16.44 mmol, 3.05 equivalent amount to R-BocHP), benzyl chloride of 0.88 g (6.95 mmol, 1.29 equivalent amount to R-BocHP) was added and stirred, raised to 50° C. and

TABLE 6

| | Solvent | | Benzylation agent | | Base | | Reaction yield (%) |
|---|---|---|---|---|---|---|---|
| | Kind | Used amount | Kind | Equivalent number | Kind | Equivalent number | |
| Exampe-19 | Dimethylformamide | 6 | BnCl | 1.7 | 48% NaOH | 5 | 88.9 |
| Comparative Example-1 | Methanol | 6 | BnCl | 1.6 | 48% NaOH | 5 | 0.0 |
| Comparative Example-2 | Ethanol | 6 | BnCl | 1.6 | KOH | 5 | 10.2 |
| Comparative Example-3 | Acetonitrile | 6 | BnCl | 1.5 | 48% NaOH | 5 | 47.2 |
| Comparative Example-4 | Toluene | 6 | BnCl | 1.6 | 48% NaOH | 5 | 0.0 |
| Comparative Example-5 | Tatrahydrofuran | 6 | BnCl | 1.6 | 48% NaOH | 5 | 0.0 |
| Comparative Example-6 | Tetrahydrofuran | 8 | BnBr | 1.2 | 48% NaOH | 2.5 | 5.6 |
| Comparative Example-7 | Tetrahydrofuran | 4 | BnBr | 1.2 | Sodium methylate | 1.2 | 32.8 |
| Comparative Example-8 | Tetrahydrofuran | 4 | BnBr | 1.2 | Sodium ethylate | 1.2 | 55.9 | heated for 7 hours. As a result of analysis by liquid chromatography, the yield of R-BocBHP was 100% on the basis of R-BocHP standard.

Example 21

To a mixed liquid of R-BocHP of 1.02 g (5.45 mmol), tetrahydrofuran of 1.50 g, tetra-n-butylammonium sulfate of 92.1 mg (0.27 mmol, 0.05 equivalent amount to R-BocHP) and 48% sodium hydroxide aqueous solution of 1.39 g (16.68 mmol, 3.06 equivalent amount to R-BocHP), benzyl chloride of 0.88 g (6.95 mmol, 1.28 equivalent amount to R-BocHP) was added and stirred, raised to 50° C. and heated for 7 hours. As a result of analysis by liquid chromatography, the yield of R-BocBHP was 98.6% on the basis of R-BocHP standard.

Example 22

To a mixed liquid of R-BocHP of 1.02 g (5.45 mmol), tetrahydrofuran of 1.50 g, n-dodecyltrimethylammonium chloride of 77.5 mg (0.29 mmol, 0.05 equivalent amount to R-BocHP) and 48% sodium hydroxide aqueous solution of 1.37 g (16.44 mmol, 3.02 equivalent amount to R-BocHP), benzyl chloride of 0.88 g (6.95 mmol, 1.28 equivalent amount to R-BocHP) was added and stirred, raised to 50° C. and heated for 7 hours. As a result of analysis by liquid chromatography, the yield of R-BocBHP was 98.0% on the basis of R-BocHP standard.

Example 23

To a mixed liquid of R-BocHP of 1.00 g (5.34 mmol), tetrahydrofuran of 1.50 g, tri-n-butylbenzylammonium chloride of 84.5 mg (0.27 mmol, 0.05 equivalent amount to R-BocHP) and 48% sodium hydroxide aqueous solution of 1.38 g (16.56 mmol, 3.10 equivalent amount to R-BocHP), benzyl chloride of 0.88 g (6.95 mmol, 1.30 equivalent amount to R-BocHP) was added and stirred, raised to 50° C. and heated for 7 hours. As a result of analysis by liquid chromatography, the yield of R-BocBHP was 81.1% on the basis of R-BocHP standard.

Example 24

To a mixed liquid of R-BocHP, of 15.13 g (81.77 mmol), tetrahydrofuran of 22.60 g, tetra-n-butylammonium sulfate of 1.40 g (4.12 mmol, 0.05 equivalent amount to R-BocHP) and 48% sodium hydroxide aqueous solution of 20.00 g (240.00 mmol, 2.94 equivalent amount to R-BocHP), benzyl chloride of 13.76 g (108.71 mmol, 1.33 equivalent amount to R-BocHP) was added and stirred, raised to 50° C. and heated for 7 hours. As a result of analysis by liquid chromatography, the yield of R-BocBHP was 99.1% on the basis of R-BocHP standard. While maintaining the obtained reaction liquid at a temperature in the range from 25° C. to 35° C., 35% HCl was added dropwise thereto. After completion of dropping, while maintaining 50° C., it was heated for 7 hours. As a result of analysis of the resulting reaction liquid by liquid chromatography, the yield of R-3BHP was 93.8% on the basis of R-BocHP standard.

Comparative Example 9

To a mixed liquid of R-BocHP (3.06 g, 16.34 mmol), tetrahydrofuran (18.89 g) and 48% sodium hydroxide aqueous solution (1.62 g, 19.44 mmol, 3.05 equivalent amount to R-BocHP), benzyl chloride (3.16 g, 18.47 mmol, 1.13 equivalent amount to R-BocHP) was added and stirred, raised to 50° C. and heated for 8 hours. As a result of analysis by liquid chromatography, the yield of R-BocBHP was 5.6% on the basis of R-BocHP standard.

(Production of R-3BHP Hydrochloride)

A method for production of R-3BHP.HCL powder by hydrochlorination of the R-3BHP obtained above will be described below.

Example 25

To a three-neck flask of 200 ml equipped with a thermometer, toluene of 122 g and THF of 8 g (toluene/THF=94/6 (weight ratio)) were added and stirred, hydrogen chloride gas was blown therein under ice cooling. As a result of neutralization titration, the concentration of hydrogen chloride in the above-described mixed solvent was 3.29% by weight.

This solution was sampled in a three-neck flask of 100 ml, and while ice cooling, 9.73 g of 87.2 wt % R-3BHP (concentrated liquid) (optical purity >99.8% ee.) was added dropwise for the liquid temperature to be 10° C. or less; after completion of dropping, the mixture was aged for 1 hour. The molar ratio of hydrogen chloride to R-3BHP in a system (HCl/R-3BHP molar ratio) was 0.95, the molar ratio of water to R-3BHP in a system (water/R-3BHP molar ratio) was 0.02 times by mole. After aging, crystals were precipitated, filtered in a nitrogen stream, and rinsed with an ice-cooled solvent of toluene/THF=94/6 (weight ratio). As a result of reduced-pressure drying, there was obtained a white crystal in powder form of 8.1 g (optical purity >99.8% ee., chemical purity >99.8%, chlorine content of 16.6% by weight) (crystallization yield 79.5%). This white crystal in powder form (white powder) was a non-sticky powder, filtering and recovery of the powder after drying were easy, and it was a powder with easy handling.

(Method of Water Absorption Experiment)

R-3BHP.HCl powder of 1.0 g was sampled in a petri dish of inner diameter 30 mm for the thickness to be uniform, and left still in a a thermo-hygrostat adjusted at an air temperature of 25° C. and relative humidity of 25% for 20 hours. The sample was weighed precisely before and after experiment, and water absorption was calculated from the weights according to the following formula.

$$\text{Water absorption} = \{(\text{sample weight after experiment} - \text{sample weight before experiment})/(\text{sample weight before experiment})\} \times 100(\%)$$

Examples 26, 27

An organic solvent that hydrogen chloride was dissolved was prepared in the same manner as in Example 25, and the experiment was carried out in the same manner as in Example 1 except that the concentration of hydrogen chloride in the organic solvent and molar ratio of hydrogen chloride/R-3BHP were changed, thereby to obtain a white crystal in powder form (white powder). The results of Examples 25 to 27 are shown in Table 7.

TABLE 7

| Example | Concentration of hydrogen chloride in organic solvent (wt %) | Hydrogen chloride/3BHP (molar ratio) | Water/3BHP (molar ratio) | Crystallization yield (%) | Water absorption (wt %) | Appearance |
|---|---|---|---|---|---|---|
| 25 | 3.29 | 0.95 | 0.02 | 79.5 | <0.10 | White powder |
| 26 | 2.08 | 1.12 | 0.04 | 92.1 | 0.13 | White powder |
| 27 | 3.23 | 1.19 | 0.04 | 89.2 | <0.10 | White powder |

The white powders obtained in Examples 25 to 27 were all a non-sticky powder, filtering and recovery of the powder after drying were easy, and it was a powder with easy handling. Additionally, in the above-described Examples 25 to 27, the experiments were carried out in an atmosphere of relative humidity in the range from 30 to 35%.

Example 28

To 66.74 g of a mixed solvent of toluene with THF that hydrogen chloride was dissolved being prepared in the same manner as in Example 25 (concentration of hydrogen chloride=3.46% by weight), 9.82 g of 87.2 wt % R-3BHP concentrated liquid was added, and aged. The molar ratio of hydrogen chloride/R-3BHP was 1.31. After the mixture was aged and concentrated at a temperature of 50° C. or less under reduced pressure using an evaporator, 60 g of toluene was added thereto, further concentrated at a temperature of 50° C. or less under reduced pressure using an evaporator, thereby to obtain a homogeneous solution of 12.8 g. The molar ratio of hydrogen chloride/R-3BHP in the homogeneous solution was 1.18. To this solution, 51.8 g of toluene and 3.5 g of THF were added and dissolved homogeneously at 40° C., then cooled to precipitate crystals. They were dried after filtration, and 8.65 g of a yellowish white crystal in powder form (optical purity >99.8%, chemical purity >99.8%) was obtained (yield=84.0%). The yellowish white powder obtained was a non-sticky powder, filtering and recovery of the powder after drying were easy, and it was a powder with easy handling.

Examples 29 to 31

The experiment was carried out in the same manner as in Example 28 except that the molar ratio of hydrogen chloride/R-3BHP before concentration was changed in Example 28. The results are shown in Table 8. The yellowish white powders obtained in Examples 29 to 31 were all a non-sticky powder, filtering and recovery of the powder after drying were easy, and it was a powder with easy handling. Additionally, the above-described experiments were carried out in an atmosphere of relative humidity in the range from 30 to 35%.

TABLE 8

| Example | Concentration of hydrogen chloride in organic solvent (wt %) | Hydrogen chloride/3BHP (molar ratio) Before concentration | Hydrogen chloride/3BHP (molar ratio) After concentration | Water/3BHP (molar ratio) | Crystallization yield (%) | Water absorption (wt %) | Appearance |
|---|---|---|---|---|---|---|---|
| 28 | 3.46 | 1.31 | 1.18 | 0.04 | 84.0 | <0.10 | Yellowish white powder |
| 29 | 3.46 | 1.51 | 1.15 | 0.04 | 87.4 | <0.10 | Yellowish white powder |
| 30 | 3.46 | 1.99 | 1.15 | 0.04 | 88.7 | <0.10 | Yellowish white powder |
| 31 | 3.46 | 2.95 | 1.20 | 0.04 | 82.7 | <0.10 | Yellowish white powder |

Example 32

While stirring a mixed solvent of 560 g of toluene and g of THF (toluene/THF=80/20 (weight ratio)), hydrogen chloride gas was blown therein under ice cooling. The resulting mixed solvent that hydrogen chloride was dissolved was sampled by 458 g in a 1 L recovery flask, 66.7 g of 87.2 wt % R-3BHP concentrated liquid was added thereto while ice cooling, and aged after completion of addition. The molar ratio of hydrogen chloride/R-3BHP in the system was 0.99. After aging, the mixture was raised to 15° C., and after crystals were precipitated, cooled to 5° C. They were filtered under nitrogen, and rinsed with 60 g of a mixed solvent of THF/toluene (20/80 weight ratio) while ice cooling, crystals were dried, thereby to obtain a light-yellowish white powder of 68.3 g (optical purity >99.8%, chemical purity >99.8%) (yield 94.2%). The yellowish white powder obtained was a non-sticky powder, filtering and recovery of the powder after drying were easy, and it was a powder with easy handling.

Examples 33, 34

Being similar to Example 32, the experiment was carried out in the same manner as in Example 32 except that solvent composition ratio and the molar ratio of hydrogen chloride/R-3BHP were changed. The results are shown in Table 9. The white powder obtained was a non-sticky powder, filtering and recovery of the powder after drying were easy, and it was a powder with easy handling. Additionally, the above-described experiments were all carried out in an atmosphere of relative humidity in the range from 30 to 35%.

TABLE 9

| Example | Concentration of hydrogen chloride in organic solvent (wt %) | Solvent composition, toluene/THF (weight ratio) | Hydrogen chloride/ 3BHP (molar ratio) | Water/3BHP (molar ratio) | Crystallization yield (%) | Water absorption (wt %) | Appearance |
|---|---|---|---|---|---|---|---|
| 32 | 2.90 | 80/20 | 0.99 | 0.02 | 94.2 | <0.10 | White powder |
| 33 | 4.19 | 70/30 | 1.11 | 0.02 | 97.3 | 0.10 | White powder |
| 34 | 4.19 | 80/20 | 1.20 | 0.02 | 90.5 | <0.10 | White powder |

Example 35

Being similar to Example 32, the experiment was carried out in such manner that the molar ratio of water/3BHP was changed to 0.15 times by mole by adding water in the crystallization system. As a result, a light-brown powder with a yield of 90.8% (optical purity>99.8% ee., chemical purity>99.7%) was obtained. However, the crystals obtained after filtering and drying were a state that the crystals were partially stuck, recovery was difficult, resulting in a crystal with difficult handling.

Comparative Examples 10, 11

The experiments were carried out in the same manner as in Example 25 except that the molar ratio of hydrogen chloride/R-3BHP was changed. The results are shown in Table 10. In Comparative example 10, a very small amount of precipitations was collected by filtration, but it was so small amount that analysis was difficult. In Comparative example 11, no precipitation was observed. Additionally, the above-described experiments were all carried out in an atmosphere of relative humidity in the range from 30 to 35%.

TABLE 10

| Comparative Example | Concentration of hydrogen chloride in organic solvent (wt %) | Hydrogen chloride/R-3BHP (molar ratio) | Water/3BHP (molar ratio) | Crystallization yield (%) |
|---|---|---|---|---|
| 10 | 3.11 | 1.30 | 0.04 | Very small amount |
| 11 | 3.11 | 1.50 | 0.04 | No precipitation |

Example 36

In a three-neck flask of 50 ml equipped with a thermometer, toluene of 10.0 g and THF of 0.88 g (toluene/THF=92/8 (weight ratio)) were charged, and 6.1 g of 87.2 wt % R-3BHP concentrated liquid was added therein and stirred. To this solution, hydrogen chloride gas was blown under ice cooling to be hydrogen chloride/3BHP molar ratio=1.1. Thereafter, the mixture was concentrated at 60° C. under reduced pressure using an evaporator, thereby to obtain a brownish yellow transparent solution of 6.8 g. Toluene of 10.0 g and THF of 0.80 g (toluene/THF=93/7 (weight ratio)) were added thereto, and aged overnight under ice cooling at room temperature. By being dried after filtration, a grey crystal in powder form of 4.54 g (optical purity >99.8% ee., chemical purity of 99.7%) was obtained (yield: 75.1%). The grey crystal was a non-sticky powder, filtering and recovery of the powder after drying were easy, and it was a powder with easy handling.

Comparative Examples 12 to 14

In a three-neck flask of 50 ml equipped with a thermometer, 22.1 g of toluene and 5.7 g of 87.2 wt % R-3BHP concentrated liquid were charged, and hydrogen chloride gas was blown therein under ice cooling to be hydrogen chloride/3BHP molar ratio=2.00. After aging under ice cooling, filtering and drying were carried out, but no powder precipitated.

Further, by changing the used amount of hydrogen chloride gas or crystallization solvent, the experiment was carried out in the same manner as in Comparative example 11.

Additionally, in the above-described Comparative examples 12 to 14, the experiment was carried out in an atmosphere of relative humidity in the range from 30 to 35%.

TABLE 11

| Comparative Example | Hydrogen chloride/3BHP (molar ratio) | Solvent | Water/ 3BHP (molar ratio) | Crystallization yield (%) |
|---|---|---|---|---|
| 12 | 2.00 | Toluene | 0.02 | No precipitation |
| 13 | 1.29 | Acetonitrile | 0.07 | No precipitation |
| 14 | 1.39 | 1-Butanol | 0.08 | No precipitation |

Example 37

In a three-neck flask of 100 ml equipped with a thermometer, 30.1 g of toluene and 5.7 g of 87.2 wt % R-3BHP concentrated liquid were charged, and while ice cooling, 3.2 g of concentrated hydrochloric acid was added dropwise for the internal temperature to be 13° C. or less. Next, the solvent was distilled away at 50° C. or less under reduced pressure using an evaporator, 50 g of toluene was then added and the solvent was distilled away once again. At the point when the moisture content in the concentrated liquid became 0.3% by weight or less (molar ratio of water to an optically active benzyloxypirrolidine derivative: 0.03 times by mole), toluene of 8.8 g and THF of 0.77 g (toluene/THF=92/8 (weight ratio)) were added and stirred, and crystals were precipitated. By being dried after filtration, a light-brown crystal in powder form of 4.59 g (optical purity >99.8% ee., chemical purity of 99.7%) was obtained (yield: 75.5%). The light brown crystal was a non-sticky powder, filtering and recovery of the powder after drying were easy, it was a powder with easy handling, and water absorption was 0.15 wt %. Additionally, in the above-described Example 37, the experiment was carried out in an atmosphere of relative humidity in the range from 30 to 35%.

The invention claimed is:

1. A process for production of a benzyloxypyrrolidine of the formula (2), comprising reacting a pyrrolidinol represented by the formula (1) with a benzyl halide in the presence of an alkali metal hydroxide, wherein the reaction is carried out in an aprotic polar solvent;

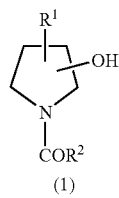

[Chemical formula 1]

(1)

wherein $R^1$ represents a group selected from i) hydrogen, ii) alkyl group and iii) aryl group; $R^2$ represents a group selected from i) hydrogen, ii) alkoxy group having carbon numbers of from 1 to 4, iii) alkenyloxy group having carbon numbers of from 2 to 4, iv) aralkyloxy group having one benzene ring, v) alkyl group having carbon numbers of from 1 to 4 and vi) aryl group having one benzene ring; and a hydroxyl group may be either 2 or 3 position of pyrrolidine ring;

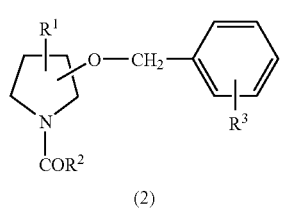

[Chemical formula 2]

(2)

wherein $R^1$ represents a group selected from i) hydrogen, ii) alkyl group and iii) aryl group; and $R^2$ represents a group selected from i) hydrogen, ii) alkoxy group having carbon numbers of from 1 to 4, iii) alkenyloxy group having carbon numbers of from 2 to 4, iv) aralkyloxy group having one benzene ring, v) alkyl group having carbon numbers of from 1 to 4 and vi) aryl group having one benzene ring; $R^3$ represents a group selected from i) hydrogen, ii) alkyl group having carbon numbers of from 1 to 4, iii) alkoxy group having carbon numbers of from 1 to 4 and iv) halogen group.

2. A process for production of a benzyloxypyrrolidine of the formula (3), wherein the benzyloxypyrrolidine obtained by the process of claim 1 is treated with an acid:

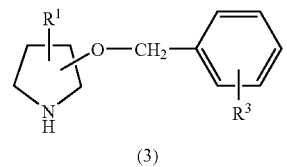

[Chemical formula 3]

(3)

wherein $R^1$ represents a group selected from i) hydrogen, ii) alkyl group and iii) aryl group; and $R^3$ represents a group selected from i) hydrogen, ii) alkyl group having carbon numbers of from 1 to 4, iii) alkoxy group having carbon numbers of from 1 to 4 and iv) halogen group.

3. The process for production of a benzyloxypyrrolidine of claim 2, wherein the benzyloxypyrrolidine of the formula (3) has the formula (4):

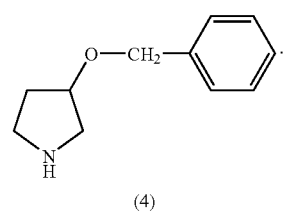

[Chemical formula 4]

(4)

4. The process for production of a benzyloxypyrrolidine of claim 1, wherein the aprotic polar solvent is dimethylsulfoxide.

5. A process for production of a hydrochloride of an optically active benzyloxypyrrolidinede of the formula (6) in the form of a powder, comprising: a first step of hydrochlorinating an optically active benzyloxypyrrolidine of the formula (5) by contacting the optically active benzyloxypyrrolidine with hydrogen chloride; and a second step of isolating the powder of the hydrochloride of the optically active benzyloxypyrrolidine by crystallizing the solution obtained by the first step, wherein a molar ratio of hydrogen chloride present in the system to the optically active benzyloxypyrrolidine is adjusted to from 0.9 to 1.2 by optionally concentrating said solution, and then crystallizing said solution:

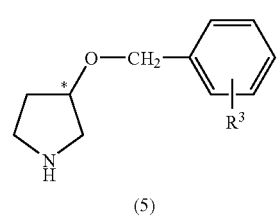

[Chemical formula 5]

(5)

wherein $R^3$ represents a group selected from i) hydrogen, ii) alkyl group having carbon numbers of from 1 to 4, iii) alkoxy group having carbon numbers of from 1 to 4 and iv) halogen group; and * in the formula represents an asymmetric carbon;

[Chemical formula 6]

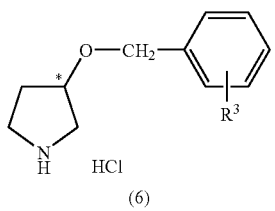

(6)

wherein R³ represents a group selected from i) hydrogen, ii) alkyl group having carbon numbers of from 1 to 4, iii) alkoxy group having carbon numbers of from 1 to 4 and iv) halogen group; and * in the formula represents an asymmetric carbon.

6. The process for production of the powder of a hydrochloride of an optically active benzyloxypyrrolidine of claim 5, comprising preparing an organic solvent having hydrogen chloride dissolved therein by contacting a hydrogen chloride gas with the organic solvent, and contacting, in said first step, the optically active benzyloxypyrrolidine with the organic solvent having the hydrogen chloride dissolved therein.

7. The process for production of the powder of a hydrochloride of an optically active benzyloxypyrrolidine of claim 5, wherein in crystallization in the second step, water present in the system is 0.1 times by mole or less relative to the optically active benzyloxypyrrolidine.

8. The process for production of the powder of a hydrochloride of an optically active benzyloxypyrrolidine of claim 5, wherein the solvent for crystallization in the second step is a mixed solvent of a hydrocarbon and an aliphatic ether.

9. A hydrochloride of an optically active benzyloxypyrrolidine of the formula (7) in the form of a powder, wherein water absorption when standing still at a relative humidity of 25% and a temperature of 25° C. for 20 hours is 0.5% by weight or less:

[Chemical formula 7]

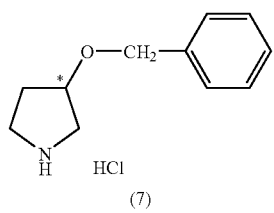

(7)

wherein * represents an asymmetric carbon.

* * * * *